United States Patent
Xu et al.

(10) Patent No.: US 10,821,412 B2
(45) Date of Patent: Nov. 3, 2020

(54) METHOD FOR GRANULATING, FORMING, AND DRYING FAT SOLUBLE NUTRIENT MICROCAPSULE PARTICLES

(71) Applicant: Zhejiang Medicine Co., Ltd. Xinchang Pharmaceutical Factory, Xinchang County (CN)

(72) Inventors: Xinde Xu, Xinchang County (CN); Bin Shao, Xinchang County (CN); Di Zhou, Xinchang County (CN); Lihua Zhang, Xinchang County (CN)

(73) Assignee: Zhejiang Madicine Co., Ltd. Xinchang Pharmaceutical Factory, Zhejiang (CN)

( * ) Notice: Subject to any disclaimer, the term of this patent is extended or adjusted under 35 U.S.C. 154(b) by 254 days.

(21) Appl. No.: 15/767,696

(22) PCT Filed: Oct. 12, 2015

(86) PCT No.: PCT/CN2015/000689
§ 371 (c)(1),
(2) Date: Apr. 12, 2018

(87) PCT Pub. No.: WO2017/063102
PCT Pub. Date: Apr. 20, 2017

(65) Prior Publication Data
US 2019/0193042 A1 Jun. 27, 2019

(51) Int. Cl.
*B01J 13/04* (2006.01)
*A23P 10/30* (2016.01)
*A61K 9/50* (2006.01)

(52) U.S. Cl.
CPC ............. *B01J 13/043* (2013.01); *A23P 10/30* (2016.08); *A61K 9/5036* (2013.01); *A61K 9/5052* (2013.01); *A61K 9/5057* (2013.01); *A61K 9/5089* (2013.01); *B01J 13/04* (2013.01)

(58) Field of Classification Search
CPC ...................................................... B01J 13/043
See application file for complete search history.

(56) References Cited

FOREIGN PATENT DOCUMENTS

CN 104306353 * 1/2015

OTHER PUBLICATIONS

Machine translation of CN 104306353.*

* cited by examiner

*Primary Examiner* — Larry W Thrower
(74) *Attorney, Agent, or Firm* — Christopher Casieri

(57) ABSTRACT

The present invention provides a method for drying high-stability microcapsule particles containing multiple double bonds fat soluble nutrients comprises: a) preparing a microcapsule emulsion containing multiple double bonds fat soluble nutrients, performing spray granulation on the microcapsule emulsion in a spray system (1), and meanwhile blasting air into the spray system (1), the blasted air wrapping adsorption materials, and the microcapsule emulsion being immediately solidified and sized after coming into contact with the air, so as to obtain liquid droplets having surfaces to which adsorption materials are adsorbed; b) performing fluidized drying on the liquid droplets having surfaces to which the adsorption materials are adsorbed in the step a) in a multi-stage fluidized bed system (5); c) collecting non-adsorbed adsorption materials by means of an adsorption material dust removal, recovery and circulation system; and d) collecting microcapsule particle products.

6 Claims, 1 Drawing Sheet

METHOD FOR GRANULATING, FORMING, AND DRYING FAT SOLUBLE NUTRIENT MICROCAPSULE PARTICLES

FIELD OF THE INVENTION

The present invention relates to a method for granulating, forming and drying fat soluble nutrient microcapsule particles. In particular, the method of the present invention is to continuously heating up easily oxidized fat-soluble microcapsule particles creatively by using an external multistage starch fluidized bed so as to make granulated microcapsule particles to be dried and molded in less time, and the dried microcapsule particles have good stability without bad smell.

BACKGROUND OF THE INVENTION

As people pay attention to their health, more and more people would like to daily take some vitamins and healthy dietary components to keep their health. These vitamins and healthy dietary components include fat-soluble nutrients such as VA, VE, and VD3; polyunsaturated fatty acids such as ω-3, ω-6, and ω-9; carotenoids such as beta-carotene, lutein, zeaxanthin, astaxanthin, ycopene, and curcumin; as well as retinoids such as coenzymes Q10.

Because of containing multiple double bonds in molecular structures of these nutrients, these nutrients have health functions. These double bonds can highly eliminate free radicals in human body and have antioxidant ability. Free radical is one of the most important reasons of producing aging and other diseases. It was estimated that 80%-90% of aging and degenerative diseases are associated with free radicals, wherein these diseases include cancer, Alzheimer's disease, Parkinson's disease, skin spots deposition, cataract, heart disease and so on. So it is of great importance for keeping body healthy and young to eliminate harmful free radicals.

These nutrients have the following structure and efficacy:

Vitamin A

Vitamin A is a very important member in fat-soluble nutrients family and has a very important function on visual health, bone health, reproduction and cell division and reproduction. It would be inconceivable for the lack of vitamin A in the human body. Vitamin A mainly exists in the form of vitamin A alcohol, vitamin A acetate and vitamin A palmitate.

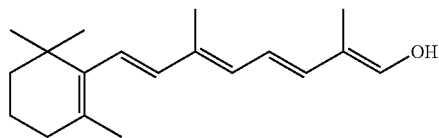

Vitamin A alcohol

Vitamin E

Vitamin E is an important anti-oxidation agent derived from nature and synthesis. Vitamin E exists in eight forms of monomers such as alpha-vitamin E, beta-vitamin E, gamma-vitamin E, and delta-vitamin E, each of the monomers has two different optical isomers. Alpha-Vitamins E including such as free type tocopherol, tocopherol acetate, tocopherol succinate and tocopheryl nicotinate are widely used in the market.

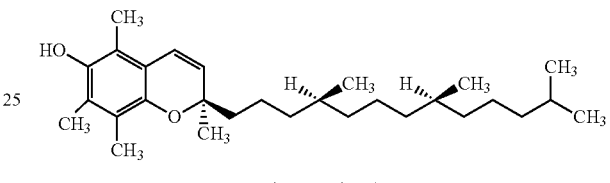

d-a-tocopherol

Polyunsaturated Fatty Acids (PUFA)

Polyunsaturated fatty acids are essential for human body and mainly plays a role on physiological functions such as maintaining cell membrane fluidity to assure normal physiological function of cells, promoting cholesterol esterfication, reducing cholesterol and triglycerides levels of blood, decreasing blood viscosity, and improving blood circulation, increasing activity of brain cells and enhancing memory and improving human thinking.

Polyunsaturated fatty acids mainly comprises ω-3 PUFA such as α-linolenic acid, Eicosapentaenoic acid, Docosahexaenoic acid and docosapentaenoic acid and ω-6 PUFA such as Linoleic acid, Conjugated Linoleic acid, γ-Linolenic, Arachidonic Acid. The molecular structures of these polyunsaturated fatty acids are as follows:

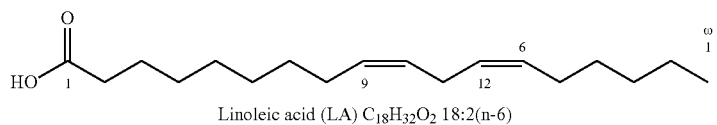

Linoleic acid (LA) $C_{18}H_{32}O_2$ 18:2(n-6)

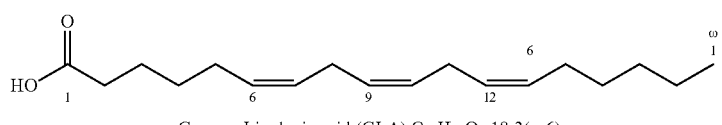

Gamma-Linolenic acid (GLA) $C_{18}H_{30}O_2$ 18:3(n-6)

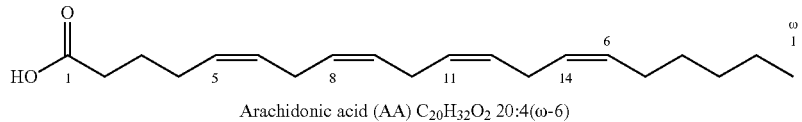

Arachidonic acid (AA) $C_{20}H_{32}O_2$ 20:4(ω-6)

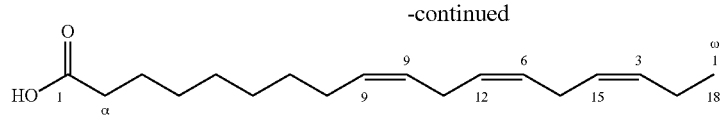

Alpha-linolenic acid (ALA) $C_{18}H_{30}O_2$ 18:3(n-3)

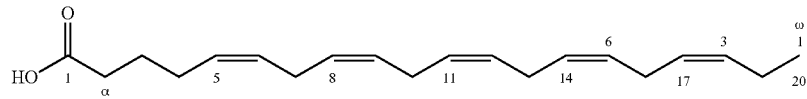

Eicosapentaenoic acid (EPA) $C_{20}H_{30}O_2$ 20:5(n-3)

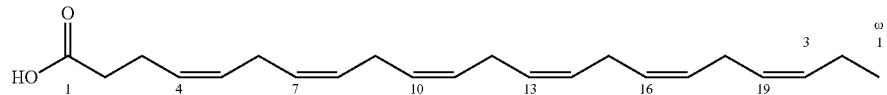

Docosahexaenoic acid (DHA) $C_{22}H_{32}O_2$ 22:6(ω-3)

The fish oils derived from abyssopelagic fishes such as anchovy, tuna and squid mainly comprise polyunsaturated fatty acids EPA and DHA. DHA and EPA are also derived from cultured algae.

Carotenoids

Carotenoids are synthesized by plants and exist in nature in the form of pigments. There are more than 600 kinds of known carotenoids, wherein beta-carotenoids, lycopene, astaxanthin, lutein and cryptoxanthin are more important carotenoids. Some carotenoids can be converted to Vitamin A having physiological effects on human body and animal body and thus are called as "provitamin A".

Carotenoids have main functions as follows: the most effective antioxidants against free radicals; enhancing immune system, increasing resistibility; preventing or fighting against cancer; decreasing risks of oral cancer, breast cancer, cervical cancer, lung cancer, trachea cancer, esophagus cancer, stomach cancer, bladder cancer; preventing heart and vascular diseases; preventing cataract, protecting fiber parts of eyes crystal; improving urinary system, preventing prostate problem; improving tendonitis and adhesive capsulitis caused by rheumatic arthritis tendinitis, being natural eye drops, maintaining lubrication and transparency of cornea and promoting health of eyes; being the precursor of VA, keeping healthy of skin and organ cavity mucosa.

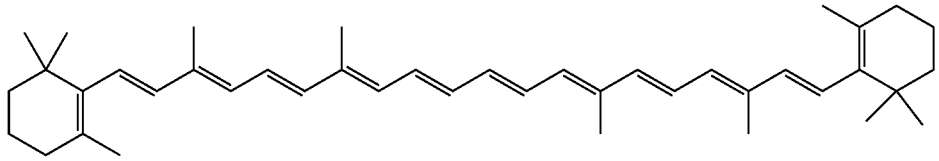

β-carotene ($C_{40}H_{56}$, M = 536.88)

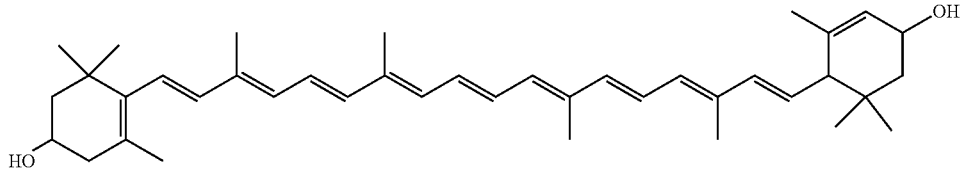

lutein ($C_{40}H_{56}O_2$, M = 568.88)

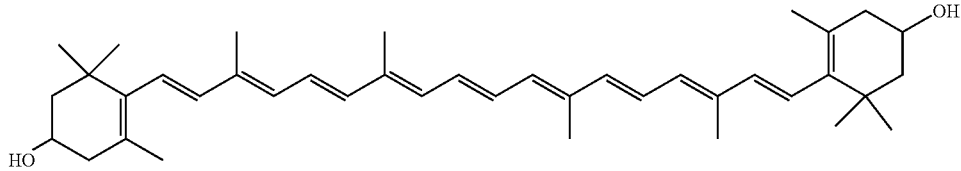

zeaxanthin ($C_{40}H_{56}O_2$, M = 568.88)

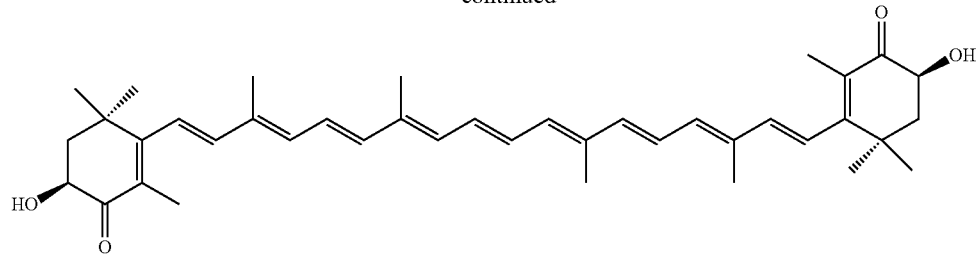

Astaxanthin ($C_{40}H_{52}O_2$, M = 596.88)

Curcumin

Curcumin is very prospective nutrients and has such functions as oxidation resisting, scavenging free radicals, anti-inflammatory, anti-freezing, regulating blood lipid, anti-lipid peroxidation, inhibiting formation of plaque, inhibiting proliferation of vascular smooth muscle cells. Their molecular structures are as follows:

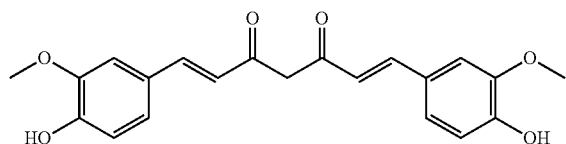

Curcumin ($C_{21}H_{20}O_6$, M = 368.4)

Coenzyme Q10

Coenzyme Q10 is a fat-soluble compound widely existed in organisms and is widely distributed in nature, mainly in yeast, plant leaves, seeds and cells of heart, liver and kidney of animals. Coenzyme Q10 is one of the most important coenzyme in human body. The main function of coenzyme Q10 is to scavenge free radicals, anti-tumor, enhance immunity, promote metabolism and improve hypoxia tolerance of heart, etc.

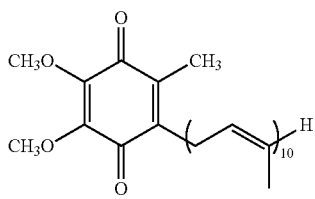

It may be seen that the above nutrients have at least two common features: 1) having fat-soluble characters, 2) having multiple double bonds in the molecular structure.

It would highly limit their application scopes and application modes due to fat-soluble characters. So their nutrients are used in the oil-based food or administered in the form of soft capsules or modified to become water soluble and thus used in the water-based foods. An important method of changing its solubility is to change fat-soluble nutrients into water soluble nutrients by microcapsule.

On the one hand, multiple double bonds provide the nutrients for antioxygenic property and scavenging free radicals and reflecting its physiological function. On the other hand, multiple double bonds make the nutrients very unstable in the storage process or in the process of microcapsule processing because of heat and light and consequently make the nutrients reduce biological activity. Especially the heating makes degradation more obvious in the case of higher temperature for long time. Sometimes it would produce many small molecule substances due to the degradation. These small molecule substances make dried microcapsule particles produce bad smell.

Many methods for preparing fat soluble nutrient microcapsules have been reported in the prior art.

US Patent No. 2007/0128341 discloses a method of preparing polyunsaturated fatty acids by lactoprotein, in particular a method of preparing polyunsaturated fatty acids microcapsule emulsion or powders from fish oils by using lactoprotein and polyunsaturated fatty acids, to obtain a microcapsule.

US Patent No. 2008/0254184 describes a formulation of preparing polyunsaturated fatty acids microcapsule using Arabic gum. But the method only uses Arabic gum as capsule shell materials. It certainly limits its application.

Chinese Patent No. 101177540B discloses a method of preparing water-soluble carotenoids microcapsule powder. In particular, carotenoids dissolved in organic solvents is mixed with water and homogenized under high pressure, high temperature and high viscosity to obtain an emulsion. A great amount of water are added for reducing the viscosity of the emulsion due to high pressure in the process. It certainly produces waste of energy and operation because of removing the water before spraying and prilling.

Chinese Patent No. 1022278257A relates to a method of preparing an algal oil DHA (Docosahexaenoic Acid) microcapsule. In particular, modified starch and Arabic gum as capsule shell materials are added in separate steps, and then an emulsifier, an aqueous phase, an emulsion phase and a combined phase, emulsion are respectively prepared. The process goes through several mixing, shearing, homogenization. And a greater amount of water are added to achieve homogenization effects. Especially it needs for removing water before spraying and drying. So the process is long and complex, low degree of efficiency.

In general, some products by the methods of preparing fat-soluble nutrients microcapsule containing multiple double bonds in the art have poor stable, fall short of expectation, complex process, lower efficiency; severe conditions. It would be very difficult to achieve in the industry. Moreover less introduction of method for granulating, forming and drying fat soluble vitamin emulsion oil-in-water is recorded in the art. A conventional method is to use a drying technique by spray drying or spray-starch bed fluidization drying to obtain microcapsule powders or particles.

In conventional spray drying process, the emulsion is subjected to a short high temperature process up to more than 180° C. Heating time of materials in the process is short. So it is easy to cause a small amount of double bonds decomposition and reduce the quality of final products and produce bad smell due to excessive high temperature. And the particle size of the obtained microcapsules is too small to easily agglomerate at redissolution. And it is easy to produce dust in packaging or application process, and consequently limit its application.

A spray-starch bed fluidization drying has been developed to overcome a limitation of conventional spray drying process. In the process, the sprayed and modeled emulsion together with low temperature starch at 20° C. are introduced into a starch fluidized bed, after spraying and modeling the emulsion containing fat-soluble vitamins. And then some moisture and starch are removed by gradually increasing starch temperature in order to finally obtain microcapsule particles wherein a layer of absorbent material is absorbed on the surface. Temperature of the starch fluidized bed must be slowly increased in order to avoid uncompletely dried microcapsule particles are redissolved at high temperature or melted on the surface to coagulate. It needs 5~6 hours to heat up about 70° C., and then dry 1~2 hours. On the one hand, it would influence appearance and roundness of particles due to fluidization for a long time. Especially, it would destroy part of fat-soluble nutrient microcapsules due to severe fluidization for a long time and then influence the stability of final products. On the other hand, long-term fluidization would lose kinetic energy and reduce a production efficiency. Further, in the whole process of granulating and molding and drying, the temperature of the microcapsule particles does not exceed 60° C. and thus no sterilization step is used in the process. But the starch could be recycled. So it could certainly bring about a problem of controlling microbials of final products and consequently it would be easy to result in excessive microorganisms in final products.

SUMMARY OF THE INVENTION

The present invention provides a method for drying microcapsule particles containing multiple double bonds fat soluble nutrients in order to overcome granulating and forming and drying deficiencies of a conventional spray-starch bed fluidized drying technology. The method comprises: a) preparing a microcapsule emulsion containing multiple double bonds fat soluble nutrients by a conventional method, performing spray granulation on the microcapsule emulsion in a spray system, and meanwhile blasting air into the spray system, the blasted air wrapping adsorption materials, and the microcapsule emulsion being immediately solidified and sized after coming into contact with the air, so as to obtain liquid droplets having surfaces to which adsorption materials are adsorbed; b) performing fluidized drying on the liquid droplets having surfaces to which the adsorption material is adsorbed in the step a) in a multi-stage fluidized bed system; c) collecting non-adsorbed adsorption materials by means of an adsorption material dust removal, recovery and circulation system; and d) collecting microcapsule particle products.

During atomization, temperature of adsorption materials is properly increased when spray forming an emulsion, and the microcapsule particles absorbed a layer of absorption materials on the surface fall into the starch fluidized bed. The starch fluidized bed is a multi-stage according to the need, and each stage of the fluidized bed has an independent air inlet system to make an inlet air temperature controlled. The inlet air temperature in each stage of the fluidized bed is gradually increased, and the microcapsule particles wrapped in starch are successively entered into each stage of the fluidized bed. In the fluidization process, most of starch will be blown away, meanwhile water is taken away to finally make the microcapsule particles dried, besides the starch absorbed on the outside of the microcapsule particles. A residence time of materials in the fluidized bed may be controlled by adjusting an inlet air temperature and air volume of different stages of the fluidized bed. For the purpose of drying, the residence time of the materials in the fluidized is generally not more than 4 hours, preferably the residence time is in a range of 1~2 hours.

"Fat-soluble nutrient having multiple unsaturated double bonds" of the present invention is referred to as a substance having double bonds in its molecular structure, being fat-soluble and in favour of the human health. The fat-soluble nutrient having multiple unsaturated double bonds is selected from the group consisting of VA, VE, natural VE, VD3, coenzymes Q10, curcumin, carotenoid and polyunsaturated fatty acid. The carotenoid is beta-carotene, lutein, astaxanthin, ycopene, and zeaxanthin; the polyunsaturated fatty acid is derived from animal extract oil, fermented source and synthetic source; the polyunsaturated fatty acid comprises conjugated linoleic acid, arachidonic acid, linoleic acid, linolenic acid, EPA, DHA and a mixture thereof. These nutrients are unstable to the heat, oxygen and light and are easily influenced by processing conditions due to these nutrients with multiple double bonds. It would produce certain degradation products, polymers or isomerization. These not only would decrease health effects of the microcapsule products, but also would produce some unpleasant odor and affect its usage.

In the present invention, the microcapsule emulsions containing fat-soluble nutrients may be prepared by conventional methods, for example, prepared by such steps as preparation of an aqueous phase, preparation of an oil phase, mixing emulsification, homogenization at high pressure, concentration and dehydration, etc.

Determining quantitatively unpleasant odor of the microcapsule powders or microparticles may be proceeded by a common electronic nose besides smelling.

Determination method: determining gas by using a broad spectrum handheld volatile organic compounds (VOC) gas detector. Type: MiniRAE 3000.

Determination step: To add 10 g sample into a jar and close a cap of the jar, and place the jar into a water bath at 60° C. for 10 min; afterwards open the cap, place a probe of the detector on the bottle mouth of the jar, and record information on odor of the sample.

The process system of the present invention comprises a spray granulation system for a fat-soluble nutrient emulsion, a fluidized drying system, an absorbent material feeding, a recovery and circulation system.

In spray granulation system, using conventional centrifugal spray atomizes and granulates the prepared fat-soluble nutrient microcapsule emulsion. Meanwhile a opening at the side of a spray granulation chamber is placed to make wind together with the adsorption materials wrapped enter into the chamber. The temperature of the inlet air is in a range of 10~90° C. according to different solidification characteristics of the capsule shell material during the preparation of microcapsule emulsions. For example, if the capsule shell material is an gelatin or other easily condensed materials, the temperature of an inlet air in the granulation chamber is higher to 90° C.; if the capsule shell material is starch sodium octenyl succinate or other difficulty condensed materials, the temperature of an inlet air in the granulation chamber is only lower to 10° C., so that the emulsion droplets immediately solidified without re-coalescence when encountering cold air, after centrifugation. After granulation, the outer surface of the emulsion droplets is adsorbed by a layer of modified starch or other adsorption materials such as silicon dioxide, phosphorus calcium silicate and phosphorus aluminum silicate and so on.

After spray granulation, the emulsion droplets adsorbed a layer of adsorption materials on the surface enter into the fluidized drying system. The fluidized drying system comprises a multi-stage fluidized bed having an independent air inlet system in each fluidized bed. The inlet air temperature may be adjusted, and the induced air outlet of each stage of the fluidized bed is finally came together. An inlet air temperature of each stage of the fluidized bed is raised in turn, hot air entered brings excess adsorption materials into a recovery system of the adsorption materials by induced air, meanwhile water in the emulsion droplets is brought into the system, to make the particles reach a dry state. According to differences of the capsule shell material in the preparation of the microcapsule emulsion and different inlet air temperature in spray granulation tower, a stage number of the fluidized bed may be selected to be 1~4 level, an inlet air temperature and a temperature difference of the fluidized bed may be optimized, such as an inlet air temperature is in a range of 20° C.~120° C., and an air inlet temperature difference is in a range of 20° C.~40° C., and an inlet air temperature of a lower fluidized bed is higher than that of an upper fluidized bed. In general, to ensure the material is dried in a shorter time, and at the same time, to make the microcapsule particles is not melted and aggregated and the particles have not been solidified at the surface due to heating up too fast. In order to ensure the materials can be smoothly entered from an upper fluidized bed into a lower fluidized bed, the pressure difference of wind in each stage of the fluidized bed can be properly maintained to ensure that the differential pressure in the pre-stage fluidized bed is higher than that that the lower stage fluidized bed.

Feeding, recycling and circulating system of the adsorption materials are also critical for normal operation of a whole system. The whole system includes an adsorption material storage, dust recovery system and a variety of pipes and so on. The adsorption materials are brought into the spray granulation tower from a storage warehouse by using wind pressures. A small amount of the adsorption materials are adsorbed on the surface of the droplet after spraying in order to prevent from reagglomeration of the droplets. Most of the adsorption materials fall into the fluidized bed with the droplet particles adsorbed the adsorption materials together, and passed into an inlet air system and induced air system of the multi-stage fluidized bed. Most of the adsorption materials are brought into a dust removal system, after gas-solid separation, to go back to the storage warehouse for recycling application.

The droplets wrapped by a layer of the adsorption materials on the surface fall into the fluidized bed after passing through the spray granulation system, and then pass through of fluidization at different temperatures, and finally recover excess adsorption materials for recycling, and the microcapsule particles are dried. In a fluidization drying process by a traditional fluidized bed, it can not only greatly reduce the fluidization time of the materials to make unstable fat soluble nutrients reduce a destruction, but also improve work efficiency, with a gradually increasing of heating temperature of the materials. Another advantage of the process different from a traditional drying process is that the temperature can be increased to 90° C., or more than 100° C. It is good for a control of materials and adsorption materials. So it would become a possibility to recycle adsorption materials.

The present invention creatively provides a multi-stage starch bed fluidized drying technology. In particular, it is properly to improve the temperature of emulsion spray forming, after the completion of atomization. A layer of the adsorption materials are adsorbed on the surface of the droplet after completing atomization, and the microcapsule particles adsorbed with the adsorption materials enter into an external fluidized bed. Difference from a traditional fluidized bed, the starch fluidized bed of the present invention is multi-stage, and the temperatures of different stages of the fluidized bed are different from a low temperature to a high temperature. A residence time of the microcapsule particles therein may be controlled by controlling the air pressure and air flow in the fluidized bed. The residence time is generally no more than 4 hours, most of them is 1~2 hours, to finally obtain the dried microcapsule particle products. The microcapsule products obtained by the process are not only stable, but also have no bad smell after being placed for a long time because of the short heating and fluidizing time. Moreover, the process time is greatly shortened, and the efficiency of labor is improved. More importantly, the microcapsule particles undergoes by a short-term high temperature before forming. It certainly plays a sterilizing role on the particles and the adsorption materials, and is favorable for microbial controls in the final products. And it has less impact on active ingredients of the microcapsule products and does not cause other negative effects because the short-term high temperature process is produced before the microcapsules but not in initial process. So it is suitable for the application in food and dietary supplements.

DETAILED DESCRIPTION AND PREFERRED EMBODIMENTS THEREOF

Hereafter, the present invention will be described specifically with reference to the examples. The examples are given only for illustration of the technical solution of the present invention and should not be construed to limit the present invention.

Example 1

Figure 1:
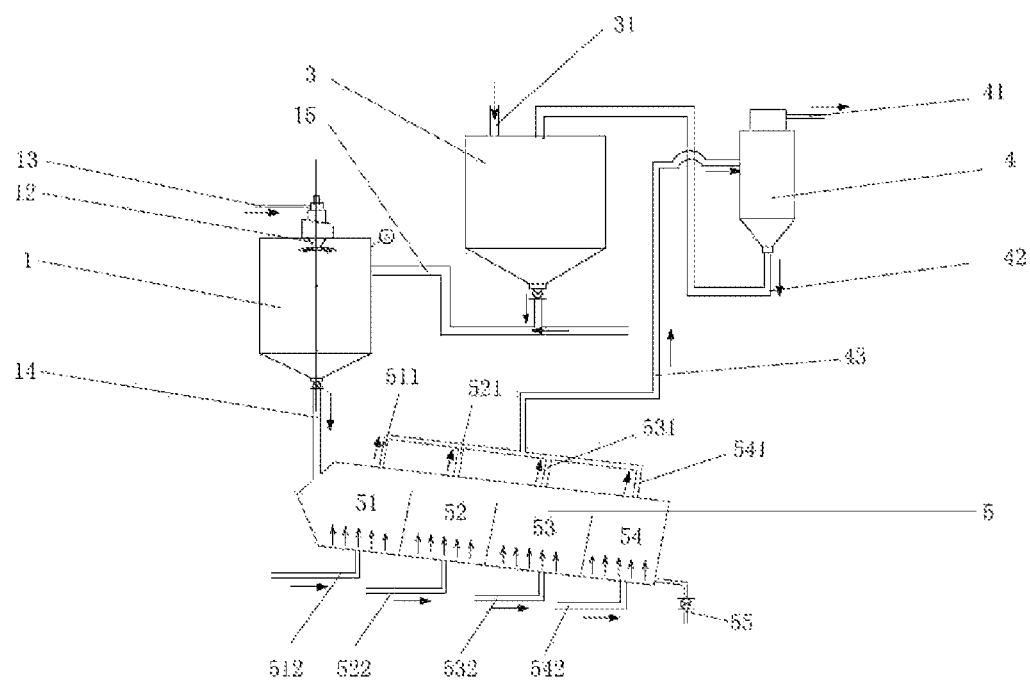
FIG. 1 shows a spray drying flow diagram of a multi-stage fluidized bed system of the present invention.

700 g fish oil ω-3 fatty acid ethyl ester emulsion (EPA 33.5%, DHA 23.1%, total content ω-3 fatty acid 59.8%) prepared, with 50% solid content, and modified starch (sodium octenyl succinate) as a capsule shell material, are added into a spray granulation system 1 through a liquid material inlet 13 of FIG. 1, to form droplets by atomization of a centrifugal nozzle 12; at the same time, blast cold air (20° C.) from a middle 15 of a spray granulation tower, the blasted air rapping modified starch (aluminum octenyl succinate), and the droplets are solidified immediately when the droplets meet cold air, and fell into the fluidized bed system 5 through the pipe 14.

The fluidized bed system comprises four stages 51, 52, 53 and 54, has corresponding air inlets 512, 522, 532, 542 and induced air inlets 511, 521, 531, 541, controlling the inlet air temperature at air inlets 512, 522, 532, 542 to be 30° C., 50° C., 70° C. and 90° C. respectively, and the modified starch brought from a modified starch storage 3 is carried and wrapped by inlet air. A differential pressure of the fluidized beds 51, 52, 53 and 54 is controlled to be 20 psi, decreasing in turn. After 2.5 hours, most of the modified starch (aluminum octenyl succinate) are introduced into the cyclone separator 4 through pipe 43, and Mark "41" is an induced air inlet of the cyclone separator. After gas-solid separation, the starch is introduced into the starch storage warehouse 3 through pipe 42 (at the beginning stage, the modified starch (aluminum octenyl succinate) is introduced into the storage warehouse through pipe 31). The dried fish oil ω-3 fatty acid ethyl ester microcapsule particles are collected by opening a valve 55. The moisture content of the particle is 5.6%. No obvious colonies are observed in the sample by microbial culture for three days.

The microcapsule particles obtained are placed in a jar with an electronic nose, to determine odor with a reading of 23.5, and the jar is incubated in a water bath at 60° C. for 10 min, then measure odor by an electronic nose with a reading of 27.6, and the odor change is not significant.

Comparative Example 2

Figure 2:
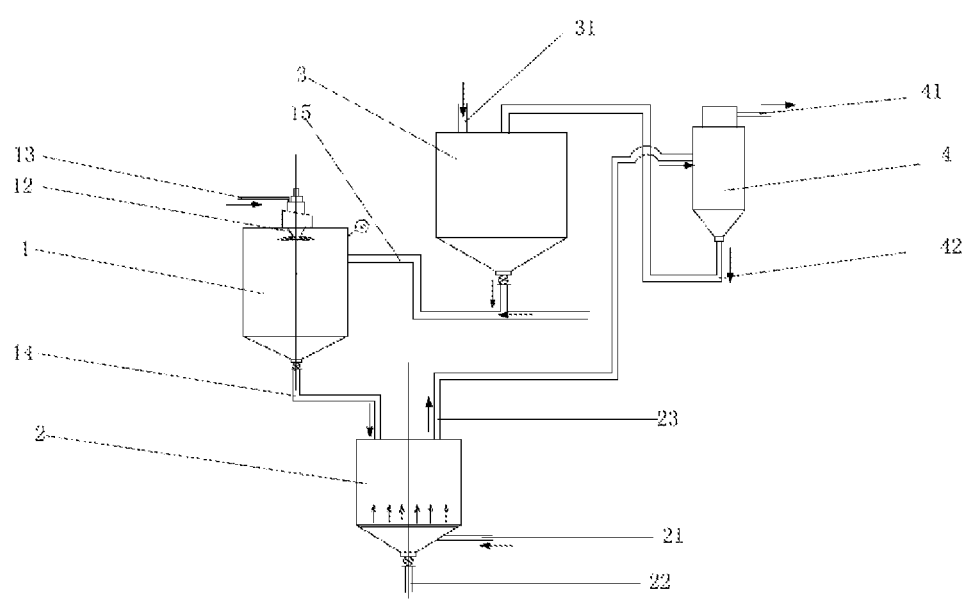
FIG. 2 shows a spray drying flow diagram of a multi-stage fluidized bed system of the prior art.

680 g fish oil ω-3 fatty acid ethyl ester emulsion (EPA 33.5%, DHA 23.1%, total content ω-3 fatty acid 59.8%) prepared, with 50% solid content, and modified starch (sodium octenyl succinate) as a capsule shell material, are added into a spray granulation system 1 through a liquid material inlet 13 of FIG. 2, to form droplets by atomization of a centrifugal nozzle 12; at the same time, blast cold air (20° C.) from a middle 15 of a spray granulation tower, the blasted air wrapping modified starch (aluminum octenyl succinate), and the droplets are solidified immediately when the droplets meet cold air, and fell into the fluidized bed system 2 through the pipe 14.

The fluidized bed system is a conventional fluidized bed system. Blow a modified starch (aluminum octenyl succinate) from an inlet air pipe 21 in order to prevent un-dried microcapsule particles from melting due to an excessively high temperature. Gradually raise an air temperature introduced from an inlet air pipe 21, starting at 20° C., and slowly rising to 70° C. after 6 hours, kept for 2.0 hours, then most of the modified starch (aluminum octenyl succinate) is introduced into the cyclone separator 4 through a pipe 23 (a pipe 22 is an outlet of the adsorption materials of less particles fluidized down), and after gas-solid separation, the starch is introduced into a starch storage warehouse 3 through a pipe 42, at the beginning stage, the modified starch such as aluminum octenyl succinate is introduced into the storage warehouse through pipe 31). The dried fish oil ω-3 fatty acid ethyl ester microcapsule particles are collected by opening a valve 55. The moisture content of the particle is 6.8%. much colonies (unreadable colonies) are observed in the sample by microbial culture for three days.

The microcapsule particles obtained are placed in a jar with an electronic nose, to determine odor with a reading of 143.2, and the jar is incubated in a water bath at 60° C. for 10 min, then measure odor by an electronic nose with a reading of 257.8, and the odor change is very significant.

It may be seen by comparison that using the multi-stage fluidized drying system of Example 1 may adjust a heating rate according to drying degree of microcapsule particles by using a stepped heating-up; meanwhile the adsorption material is gradually removed from different fluidized beds, thereby further accelerate a drying process of the materials. The whole drying process needs only 2.5 hours, the obtained product has little fishy smell, and has good stability. It is important to detect less microbial by microbial culture.

On the contrary, the condensed droplets of the comparative example 2 are treated by a conventional fluidized bed. A temperature rising procedure of the fluidized bed must be very slow in order to make solidified droplets not to be melted and aggregated because of high temperature. And a drying speed of the materials and adsorption materials are further reduced since the adsorption materials cannot be removed timely. A rising temperature time of fluidized bed from 20° C. to 70° C. is 6.0 hours, a drying time is 2.0 hours. So a total time is nearly 8.0 hours. It is more longer than 2.5 hours relative to that of the present invention, and the stability of the final particle product is obviously inferior to the microcapsule products of Example 1. And the final particle product has a obvious fishy smell. Much colonies (unreadable colonies) are observed in the sample and thus it requires an additional sterilization process.

Examples 3-8

The implement objects and related parameters of Examples 3~8 are listed in Table 2.

|  | Example 3 | Example 4 | Example 5 | Example 6 | Example 7 | Example 8 |
| --- | --- | --- | --- | --- | --- | --- |
| Types of active Ingredients in Microcapsule Emulsion | Conjugated Linoleic Acid (CLA), Linoleic Acid, Linolenic Acid | Curcumin | Astaxanthin, Lycopene, Lutein, beta-carotene | Coenzyme Q10, Reduced Coenzyme Q10 | Arachidonic Acid (AA), Algae DHA | VA, Vitamin E, Vitamin D3, Natural Vitamin E |
| capsule shell material in Microcapsule Emulsion | Gum Arabic | Gelatin | Modified Starch | Sodium Caseinate | Modified Starch | Gelatin |
| Adsorption Material | Modified Starch | Modified Starch | Calcium Phosphor Silicate | Modified Starch | Silicon Dioxide | Aluminium Phosphor Silicate |
| Inlet Air Temperature of Spray Granulation System | 45° C. | 90° C. | 30° C. | 90° C. | 10° C. | 60° C. |
| Number of Fluidized Bed Stage | 3 | 2 | 4 | 1 | 4 | 2 |

-continued

|  | Example 3 | Example 4 | Example 5 | Example 6 | Example 7 | Example 8 |
|---|---|---|---|---|---|---|
| Inlet Air Temperature of Fluidized Bed (° C.) | 60, 80, 90 | 60, 120 | 20, 40, 60, 80 | 80 | 30, 50, 80, 90 | 60, 100 |
| Fluidized Drying Time | 3.0 hr | 2.0 hr | 3.0 hr | 1 hr | 4 hr | 2.5 hr |
| Moisture Content of Final Product (Weight Percentages) | 5.7% | 5.6% | 5.2% | 8.3% | 6.5% | 7.1% |
| Total Number of Colonies in Final Products | n.d. | n.d. | n.d. | <350 cfu/g | n.d. | n.d. |

The experiment of the present invention show that the microcapsule product obtained by the drying method of the present invention has not only good stability, but also no bad smell after being placed for a long time due to a short time of heating and fluidization. Moreover, the process time is greatly shortened, and the efficiency of labor is improved.

The present invention is illustrated by the above examples, however, should understand that the present invention is not limited to special instance and implementation scheme described here. These special examples and implementation plans is aimed at helping the person skilled in the art to practice the present invention. The persons skilled in the art is easily from the spirit and scope of the present invention to further improve and perfect, so the present invention only restricts by the content and scope of the claims of the present invention, and its intention to cover all in the alternative solutions and equivalent solutions which included in appendix claim limit within the scope of the invention spirit.

The invention claimed is:

1. A method for drying microcapsule particles containing multiple double bonds fat soluble nutrients, comprising the following steps:
   a) preparing a microcapsule emulsion containing multiple double bonds fat soluble nutrients, performing spray granulation on the microcapsule emulsion in a spray system at a temperature of 10-90° C., and meanwhile blasting air into the spray system, the blasted air wrapping adsorption materials, and the microcapsule emulsion being immediately solidified and sized after coming into contact with the air, so as to obtain liquid droplets having surfaces to which adsorption materials are adsorbed;
   b) performing fluidized drying on the liquid droplets having surfaces to which the adsorption material is adsorbed in the step a) in a multi-stage fluidized bed system, wherein the number of stages of the multi-stage fluidized bed system is 1-4 level, the differential pressure between two adjacent stages of the multi-stage fluidized bed systems is 20 psi; the inlet air temperature of the multi-stage fluidized bed system is in a range of 20-120° C.; the inlet air temperature of a lower fluidized bed is higher than that of an upper fluidized bed, and the inlet air temperature difference is 20-40° C.;
   c) collecting non-adsorbed adsorption materials by means of an adsorption material dust removal, recovery and circulation system; and
   d) collecting microcapsule particle products.

2. The method according to claim 1, wherein the microcapsule emulsion comprises a fat-soluble nutrient containing multiple unsaturated double bonds and a capsule shell material.

3. The method according to claim 2, wherein the fat-soluble nutrient containing multiple unsaturated double bonds is selected from the group consisting of Vitamin A, Vitamin E, natural Vitamin E, Vitamin D3, coenzyme Q10, reduced coenzyme Q10, curcumin, carotenoids, polyunsaturated fatty acids; the capsule shell material comprises animal capsule shell material and vegetable capsule shell material.

4. The method according to claim 3, wherein the carotenoid is beta-carotene, lutein, astaxanthin, ycopene, and zeaxanthin; the polyunsaturated fatty acid is derived from animal extract oil, fermented source and synthetic source; the polyunsaturated fatty acid comprises conjugated linoleic acid, arachidonic acid, linoleic acid, linolenic acid, EPA, DHA and a mixture thereof; the animal capsule shell material is gelatin; the vegetable capsule shell material is Arabic gum, modified starch, sodium caseinates.

5. The method according to claim 1, wherein the adsorption material comprises modified starches, silicon dioxide, phosphorus calcium silicate and phosphorus aluminum silicate.

6. The method according to claim 1, wherein in step b), a fluidized drying time of the multi-stage fluidized bed system is within 4.0 hours.

* * * * *